(12) United States Patent
Anderson et al.

(10) Patent No.: US 6,831,468 B2
(45) Date of Patent: Dec. 14, 2004

(54) METHOD AND APPARATUS FOR DETERMINING MOISTURE CONTENT AND CONDUCTIVITY

(75) Inventors: Scott K. Anderson, Meridian, ID (US); Hyrum S. Anderson, Meridian, ID (US)

(73) Assignee: Technical Development Consultants, Inc., Meridian, ID (US)

( * ) Notice: Subject to any disclaimer, the term of this patent is extended or adjusted under 35 U.S.C. 154(b) by 0 days.

(21) Appl. No.: 10/659,645

(22) Filed: Sep. 10, 2003

(65) Prior Publication Data

US 2004/0059509 A1 Mar. 25, 2004

Related U.S. Application Data

(63) Continuation of application No. 10/367,688, filed on Feb. 19, 2003, and a continuation of application No. 10/367,310, filed on Feb. 19, 2003, and a continuation-in-part of application No. 09/945,528, filed on Sep. 4, 2001, now Pat. No. 6,657,443.

(51) Int. Cl.[7] .............................................. G01R 27/26
(52) U.S. Cl. ...................................... 324/664; 324/689
(58) Field of Search ................................ 324/664, 640, 324/643, 663, 689, 534; 73/29.01, 73

(56) References Cited

U.S. PATENT DOCUMENTS

| | | | | |
|---|---|---|---|---|
| 5,148,985 A | * | 9/1992 | Bancroft | 239/64 |
| 5,677,476 A | * | 10/1997 | McCarthy et al. | 73/29.01 |
| 5,818,241 A | * | 10/1998 | Kelly | 324/640 |
| 6,215,317 B1 | | 4/2001 | Siddiqui et al. | 324/643 |
| 6,340,892 B1 | * | 1/2002 | Rynhart et al. | 324/640 |
| 6,441,622 B1 | | 8/2002 | Wrzeninski et al. | 324/643 |
| 6,657,443 B2 | * | 12/2003 | Anderson | 324/664 |

* cited by examiner

*Primary Examiner*—Jay Patidar
*Assistant Examiner*—Donald M. Lair
(74) *Attorney, Agent, or Firm*—Robert A. Frohwerk; Your Intellectual Property Matters, LC

(57) ABSTRACT

Methods and apparatuses are described for detecting volumetric moisture content and conductivity in various media based on a time-domain reflectometry (TDR) system wherein successive fast transitions are injected into a transmission line immersed in a medium of interest, and a characteristic received waveform is digitized and analyzed by continuously sampling multiple received waveforms at short time intervals. One method transmits a timing signal along a shielded transmission line while a coincident signal is transmitted through the medium of interest. Another method propagates the waveform along a transmission line, that may be either shorted or open-ended, and observes a reflected, rather than transmitted, waveform with a receiver connected to the same end of the transmission line as the transmitter. The effects of dispersion caused by the conductive and dielectric properties of the medium on the waveform in an unshielded transmission line are extrapolated by detecting the bulk propagation time and the slope of the distorted rising edge of the characteristic received waveform. Absolute volumetric moisture percentage is inferred from propagation time, and absolute conductivity is inferred from the maximum slope value of the distorted rising edge of the characteristic received waveform.

30 Claims, 5 Drawing Sheets

METHOD AND APPARATUS FOR DETERMINING MOISTURE CONTENT AND CONDUCTIVITY

CROSS-REFERENCES TO RELATED APPLICATIONS

This application is a Continuation-In-Part of U.S. patent application Ser. No. 09/945,528 that was filed on Sep. 4, 2001, (now U.S. Pat. No. 6,657,443, issued on Dec. 2, 2003.

This application is also a Continuation of, and claims the benefit under 35 U.S.C. 120 of the following two co-pending U.S. Patent Applications, both of which were filed on Feb. 19, 2003, and both of which are hereby incorporated by reference in their entireties into the present disclosure:

Application Ser. No. 10/367,688 titled "Method and Apparatus for Determining Moisture Content and Conductivity", and Application Ser. No.10/367,310 titled "Digital Time Domain Reflectometry Moisture Sensor."

U.S. PATENT DOCUMENTS

U.S. Pat. No. 6,215,317 Apr., 2001 Siddiqui, et al 324/643

U.S. Pat. No. 6,441,622 Aug., 2002 Wrzeninski et al. 324/643

STATEMENT REGARDING FEDERALLY SPONSORED RESEARCH OR DEVELOPMENT

Not Applicable

SEQUENCE LISTING OR PROGRAM

Not Applicable

FIELD OF THE INVENTION

The present invention relates generally to electronic moisture sensors, and specifically to time domain reflectometry moisture sensors. This invention represents modifications and extensions to the method and apparatus for extrapolating soil moisture and conductivity disclosed in U.S. patent application Ser. No. 09/945,528.

BACKGROUND

A variety of sensors have been developed to detect moisture in various media. These include conductivity sensors, bulk dielectric constant sensors, time domain reflectometer or transmissometer (TDR or TDT) type sensors, and various oscillator devices, the majority of which exploit the high dielectric constant of water to extrapolate moisture content in the medium. In particular, TDR type sensors have been used over the past several years to measure the water content in various applications. Such applications include detecting volumetric soil moisture, determining liquid levels in tanks, and determining moisture content in paper mills and granaries.

A major setback in determining volumetric moisture content in a medium is the influence of conductive materials in the medium of interest. For example, soil conductivity is a function of the ion content of the soil and of its temperature. Salts from irrigation water and/or fertilizer can build up in the soil and cause significant errors in TDR-based moisture readings.

Because of the uncertainty in moisture readings caused by conductivity, many of the TDR sensors now available are "relative" sensors. This means that the sensor does not report absolute moisture content readings, but uses reference points obtained through testing. In essence, the moisture sensor does not report absolute moisture content readings, but reports a "wetter than" or "drier than" condition based on the relative difference of the conductivity-dependent moisture content reading and the reference reading.

Unfortunately, the readings from these "relative" sensors do not remain in synchronism with the true or "absolute" water content of the medium, but fluctuate with time. For example, the salinity (ionic content) of soil may fluctuate with season. In such a case, the original reference point becomes an inaccurate indicator of the moisture level of the medium.

The method and apparatus disclosed in U.S. patent application Ser. No. 09/945,528 ('528) provide a way to report absolute volumetric water content of a medium. This is done by essentially analyzing the distortion effects on a transmitted waveform caused by the properties (namely conductivity and dielectric constant) of the medium. The '528 disclosure provides a means to launch a fast rising positive edge onto a transmission line passing through a specific length of soil. The previously disclosed embodiment and associated method may be modified to suit other configurations and implementations so as to more readily adapt the technique to other media in addition to soil. In a first set of alternatives, since the described system includes both a transmitter and receiver, some variations may be made in how the transmitter and receiver are physically related to one another within the moisture sensing system. A second set of alternative configurations, independent of the first, derives from variations in the manner in which the transmission line is terminated.

The embodiment described in '528 uses a transmission line that folds back to a receiver mounted on the same circuit board as the transmitter. As a result of housing the transmitting and receiving electronics on the same circuit board, and folding the transmission line, feed-through noise is inherent in the characteristic received waveform. One possible variation from the previously described embodiment is to incorporate what may be referred to as a Bi-static approach.

With the Bi-static approach the transmitting and receiving circuitry are housed on separate circuit boards, connected by a straight unshielded transmission line used for sending the successive waveforms, a shielded transmission line used for timing, and a wire bundle for communication and power purposes. This eliminates the feed-through noise in the characteristic received waveform, resulting in a simpler detection scheme for bulk propagation delay and distorted rising edge slope.

Another alternative embodiment uses a reflected wave rather than the transmitted one. When using the reflected wave approach the transmitter launches a step function at one end of a transmission line, the other end of which may be either shorted or open-ended. The fast rising step function propagates along the line and is reflected at the shorted or open end back to the point of origin. A receiver samples and digitizes the returning waveform into closely spaced digital samples representing the amplitude at precise time intervals of the returned waveform. Analysis of these samples yields an accurate measurement of the round-trip propagation time of the step function, even in the presence of waveform distortion caused by conductive elements in the medium surrounding the transmission line. From the propagation time the bulk dielectric constant of the medium can be determined and from that the volumetric moisture content of the medium. Further analysis of the distortion of the waveform yields the bulk electrical conductivity of the medium.

BRIEF SUMMARY OF THE INVENTION

The disclosed invention is a method and apparatus for inferring volumetric moisture content and bulk conductivity of a medium of interest using a TDR-based system after the manner of the disclosure in '528. The present invention describes alternative embodiments which use a Bi-static approach in one instance, and reflected wave approaches in other instances, to measure the propagation time.

In all embodiments as in '528, a very precise timing and successive approximation amplitude-measuring scheme captures the timing of the received waveform with picosecond resolution and its amplitude with millivolt resolution. From point-by-point measurements, the characteristic received waveform is examined. Propagation delay of the characteristic received waveform is set as the first time when the amplitude of the received waveform is greater than a threshold. This information is used to infer the bulk dielectric constant of the moisture-bearing medium. The maximum slope of the characteristic received waveform is also examined and used to infer conductivity of the medium under test.

DETAILED DESCRIPTION

The particular apparatus disclosed in patent application Ser. No. 09/945,528 ('528) may be modified in various manners. One modification physically separates the transmitting and receiving units; this will be referred to as the Bi-Static approach. Another independent set of modifications allow the transmitting and receiving units to be connected to the same end of the open or shorted transmission line, rather than to opposite ends. These are TDR (Time Domain Reflectometric) methods and will be discussed as such. For each such modified system, the method of extracting propagation delay and maximum slope are slightly different due to the inherent difference in the characteristics of the received waveform.

Bi-Static Approach

Figure 1:
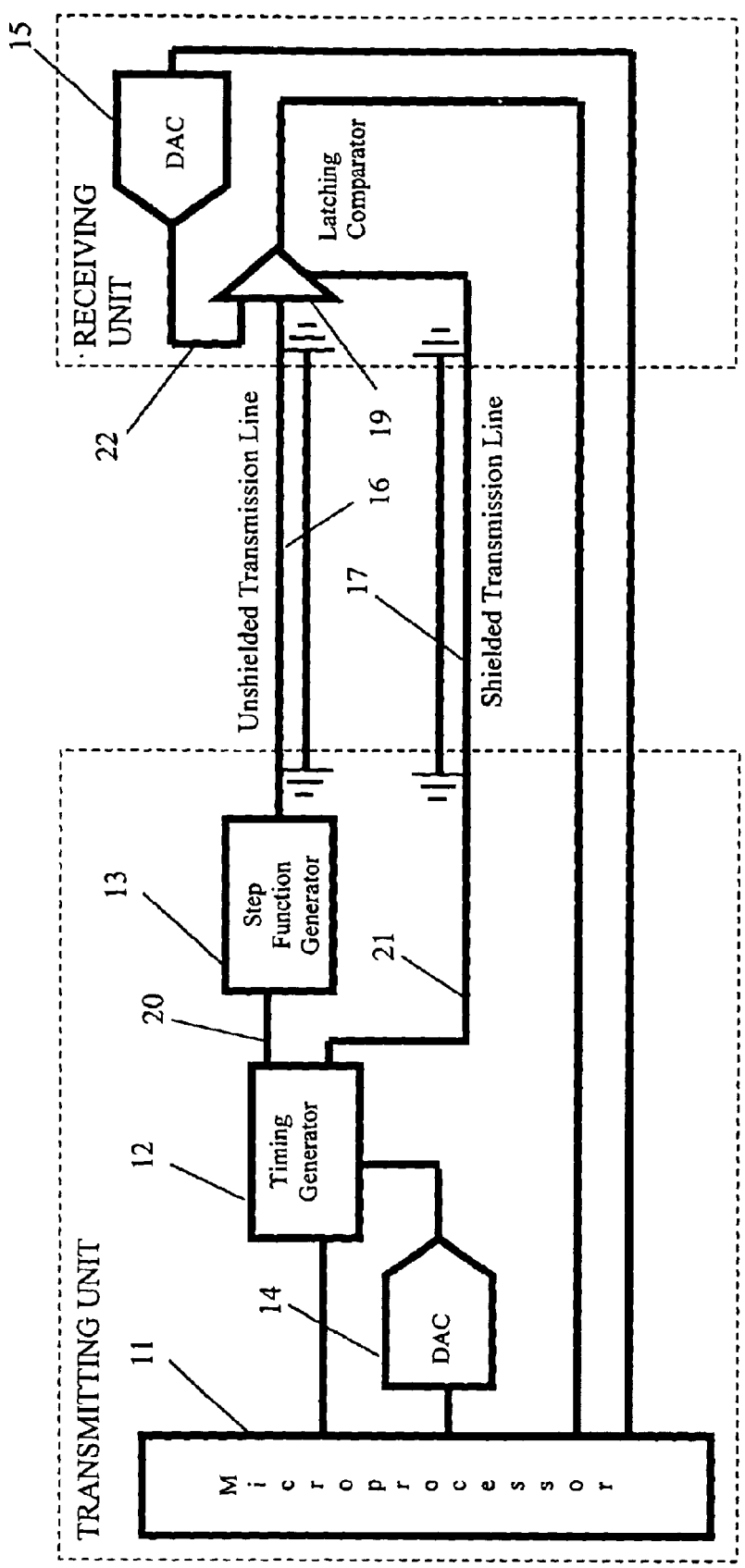
FIG. 1 is a simplified block diagram of a Bi-static sensor system.

The important elements of a moisture sensor using the Bi-static approach are diagrammed in FIG. 1. This figure is a simplified block diagram of a precisely timed waveform generator coupled with a successive approximation amplitude measurement system capable of capturing the detail of very fast waveforms. An electrical circuit schematic of one implementation of such a measurement system has been shown in '528.

The timing generator 12 provides two trigger signals on outputs 20 and 21 that are precisely separated in time by a programmable offset ranging from zero to tens of nanoseconds with a resolution of tens of picoseconds. In the preferred embodiment the offset amount is governed by the setting of a first digital to analog converter (DAC) 14 as described in '528. The author recognizes that the disclosed method is only one of many techniques for generating programmable time offsets. Other methods include but are not limited to programmable delay lines, programmable frequency synthesizers and programmable pulse width generators.

The first trigger output 20 activates a step function generator 13 that serves as a transmitter. The output of step function generator 13 is a very fast rising edge that propagates down an unshielded transmission line 16 to a latching comparator 19 that acts as a receiver. A second DAC 15 establishes a voltage reference level 22 to drive the other input of the latching comparator 19. The delayed second trigger output 21 from timing generator 12 is sent down a shielded transmission line 17; the shield serving to isolate the signal from its surroundings so that the speed of propagation is independent of the properties of the medium of interest.

If the incoming waveform from the unshielded transmission line 16 is higher in amplitude than voltage reference level 22 at the time that the second trigger output 21 arrives via shielded transmission line 17, then the latching comparator 19 provides a logical '1' output. If the amplitude of the incoming waveform is lower than the voltage reference level 22 presented by the setting of the second DAC 15, the latching comparator 19 provides a logical '0' output. The state captured by the latching comparator 19 is examined by the microprocessor 11. These features make it possible to measure the amplitude of the incoming waveform at a precise time after the waveform was launched. By repeatedly measuring the waveform amplitude at successive time increments, the entire waveform can be reconstructed. This reconstructed waveform is referred to hereafter as the characteristic received waveform. It will be noted though that the moisture-sensing methods described here do not require reconstruction of the entire waveform.

Measuring the amplitude of the characteristic received waveform at a given point in time is accomplished through a successive approximation technique requiring a sequence of waveform launch and receive cycles. The number of cycles required is equal to the number of bits of resolution in the voltage reference level DAC 15. First, the microprocessor 11 sets the timing offset DAC 14 to establish a desired time delay between the two trigger outputs 20 and 21. This setting represents the time after the launch of the waveform by step function generator 13 onto unshielded transmission line 16 at which the received waveform will be sampled at latching comparator 19. This setting will remain fixed while the amplitude at this point is found.

Next, the voltage reference level DAC 15 is set to half scale, that is, the most significant bit is set and all other bits are cleared. Then an output from the microprocessor 11 starts the timing generator 12. The first trigger output 20 from the timing generator 12 causes the step function generator 13 to launch a step onto unshielded transmission line 16. At the precisely programmed interval later, the second trigger output 21 is sent down the shielded transmission line 17 and latches the input to the receiver, latching comparator 19. It is noted that the latching actually occurs at the programmed offset plus the time required for the signal to travel down the shielded transmission line 17, which is a known quantity.

Next, the microprocessor 11 examines the output of latching comparator 19. If it is a logical '1', as occurs when the transmitted waveform is higher in amplitude than the voltage reference level DAC 15, then the microprocessor 11 leaves the bit most recently set in its set state and proceeds to set the next most significant bit. If latching comparator 19 indicates a logical '0' output, due to the transmitted waveform being lower in amplitude than the voltage reference level DAC 15, then the microprocessor 11 clears the bit most recently set before setting the next lesser significant bit. Then another step function is launched onto unshielded transmission line 16. This sequence is repeated until all bits in the voltage reference level DAC 15 have been successively processed from the most significant to the least significant. The resultant input setting to the voltage reference level DAC 15 is the digital representation of the waveform amplitude at the precise time that was loaded into the timing offset DAC 14.

Figure 2:
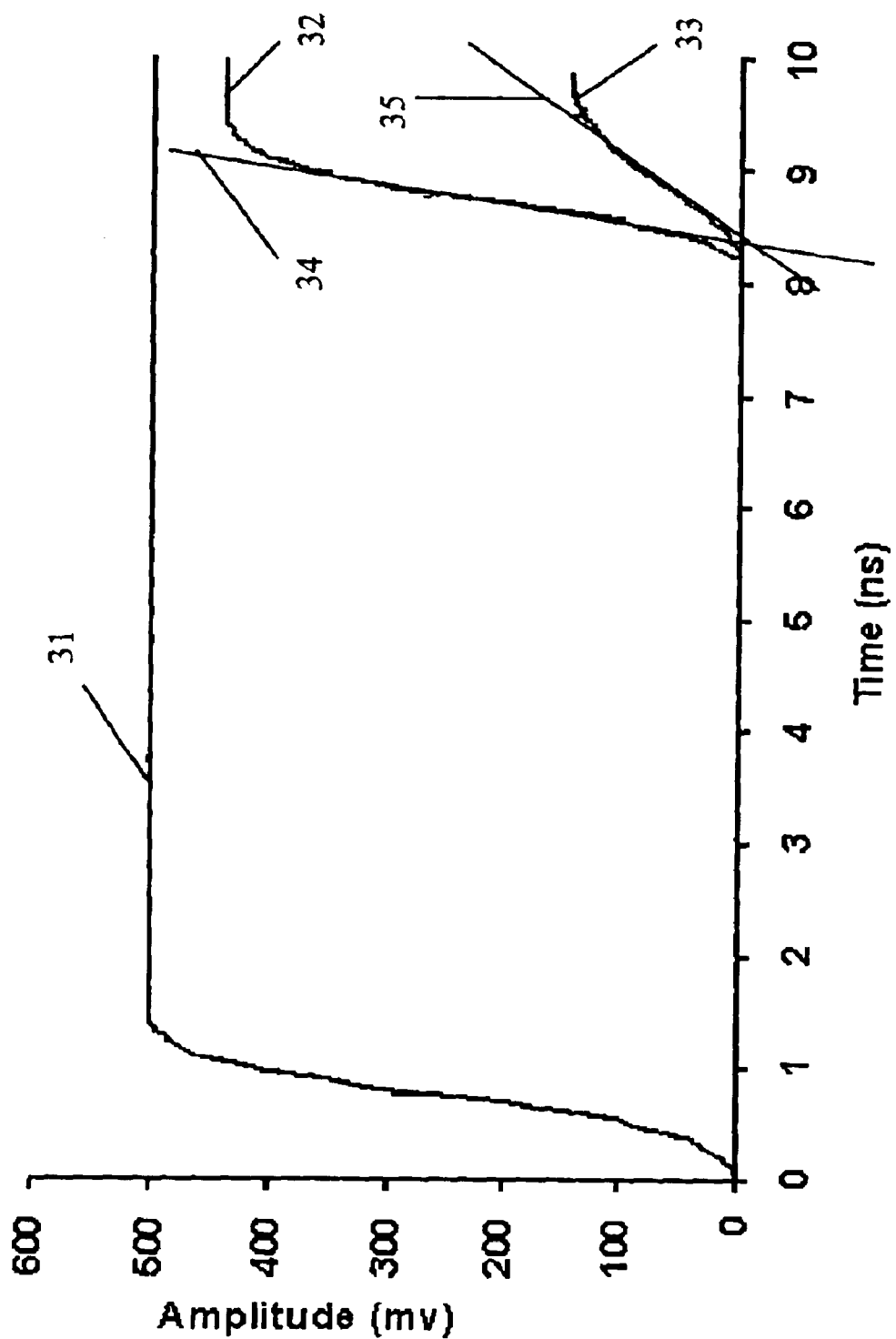
FIG. 2 shows typical waveforms encountered in a Bi-static sensor system.

FIG. 2 represents waveform measurements taken at successive time increments using the aforementioned process. The transmitted waveform 31 represents the output from the step function generator 13. Received waveform 32 represents the portion of the characteristic received waveform that has propagated through moist soil, or another medium, that has low conductivity. Note that received waveform 32 is essentially the same as transmitted waveform 31 except that it has been translated to the right, that is, delayed in time, and its amplitude is slightly lower. Note that in the apparatus described in '528, a low level signal preceded the transition in the characteristic received waveform, indicating residual feed-through due to the transmitter and receiver residing on the same circuit board. In this present disclosure using the Bi-static approach, no feed-through is observed since the first signal component to reach the latching comparator 19 (of FIG. 1) at the receiving end is the waveform that was sent down the unshielded transmission line 16.

Received waveform 33 represents the characteristic received waveform that has propagated through moist soil, or another medium, having high conductivity. Note that received waveform 33 differs from received waveform 32 in that the rising edge slope is not as steep. However, the propagation times are nearly identical. This is expected since received waveforms 32 and 33 represent characteristic received waveforms that have propagated through media of equal wetness, but different conductivities.

For a given characteristic received waveform, the bulk dielectric constant and the conductivity of the medium of interest may be determined in a few ways. First, since there is no feed-through in the characteristic received waveform 32, propagation may be inferred as that time when the amplitude of waveform 32 is greater than some threshold. This threshold may be set to a value above the noise floor of the receiving system and below a value that would cause significant error in the time to propagate through conductive media.

Second, the propagation time may be calculated by projecting the maximum slope of the waveform onto the zero-Volt line (x-axis). This point of intersection represents the estimated propagation time. As described in '528, the slope of the line having maximum slope can be used to infer conductivity.

A third way to determine propagation delay is by computing the second derivative. The major point of inflection corresponds to the bulk propagation time.

Since it is desirable to know the maximum slope in order to calculate conductivity, the authors have chosen to implement the second of the above methods. This method is also advantageous since the point at which maximum slope occurs is when most of the energy of the transmitted waveform is reaching the receiving end, hence at this point the greatest signal to noise ratio occurs, assuming stationary noise statistics. The slope amplitude (Volts/second) and temporal position (seconds) are accurate and repeatable.

The maximum slope of the characteristic received waveform is located in the following manner. Since we expect that the characteristic received waveform will contain noise, a first derivative approximation is incorporated to provide smoothing. To approximate the derivative at each point, a thirty-two point window of data is stored. The first derivative approximation at a point in the center of the window is calculated as the sum of the second sixteen entries minus the first sixteen entries, divided by the sum of all thirty-two entries.

A search for the maximum slope begins at a time when the characteristic received waveform is greater than some voltage above the waveform. The maximum slope, its temporal location, and the amplitude at that location are stored. Propagation time is then determined by projecting the maximum slope line 34 onto the zero-Volt baseline (x-axis) and noting the point of interception. Following the same procedure in a more conductive media will give the maximum slope line 35, which intercepts the baseline at the same point, indicating a consistent propagation time without regard to conductivity.

TDR Methods

Figure 3:
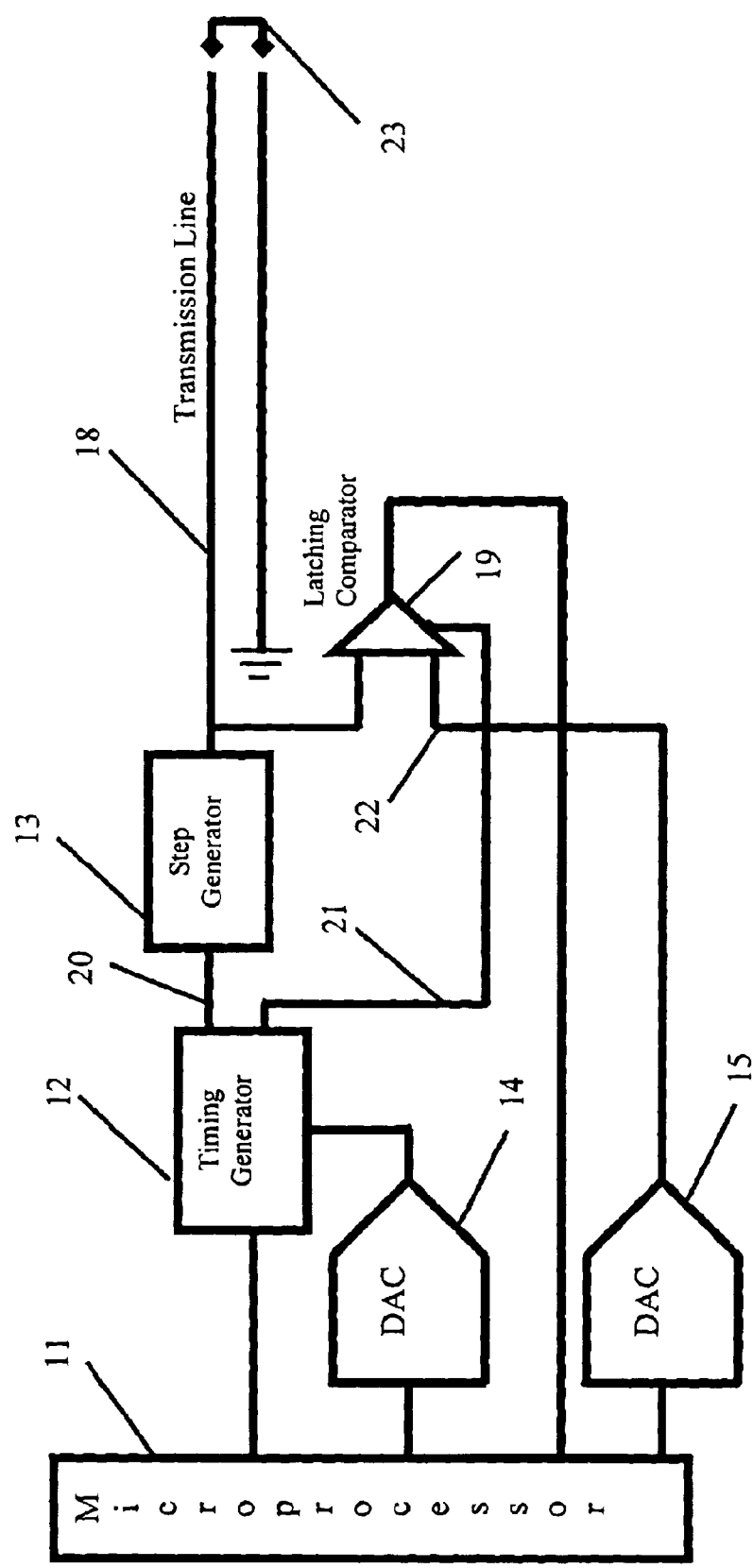
FIG. 3 is a simplified block diagram of a TDR sensor system.

As shown in FIG. 3, the important elements of a moisture sensor using a TDR method are very much the same as shown in FIG. 1 for the Bi-Static approach, but reorganized slightly. The timing generator 12 again provides two trigger outputs 20 and 21 which are precisely separated by a programmable time offset, governed by timing offset DAC 14, ranging from zero to tens of nanoseconds with a resolution of tens of picoseconds.

The first trigger output 20 activates a step function generator 13. The output of this step function generator 13 propagates down transmission line 18 to the distal end where an optional shorting bar 23 may be installed. Whether transmission line 18 is open-ended or shorted, the signal will be reflected and returned to the receiver, latching comparator 19. The primary difference between the TDR method and the above-described Bi-Static approach is that the latching comparator 19 is connected to the transmission line 18 at its proximal end, the same end that is driven by step function generator 13, rather than at its distal end. The second trigger output 21 is applied to the latch input of the latching comparator 19.

Depending upon whether the waveform amplitude at the driving and receiving end of the transmission line 18 is higher or lower in amplitude than the voltage reference level DAC 15 driving the other input at the time of the second trigger output 21, the latching comparator 19 will provide a logical '1' or logical '0' output, respectively. The state captured by latching comparator 19 is then examined by the microprocessor 11, which adjusts the voltage reference level DAC 15 and launches successive step functions until the amplitude of the characteristic received waveform at the time of the second trigger output 21 has been acquired. Then the timing offset DAC 14 can be adjusted to move the second trigger output 21 to the next time increment so that the amplitude at that point in time can be digitized. As in other described configurations, repeated measurements of the waveform amplitude at successive time increments allow the entire characteristic received waveform to be reconstructed, though it need not be.

Measurement of the amplitude of the characteristic received waveform is accomplished through a successive approximation technique similar to that described above for the Bi-static approach. In the TDR method, however, the fact that the receiver, latching comparator 19, has been relocated from the distal to the proximal end of the transmission line 18 means that the second (shielded) transmission line (17 of FIG. 1) has been replaced by a direct connection between the second trigger output 21 from the timing generator 12 and the latching comparator 19.

Figure 4:
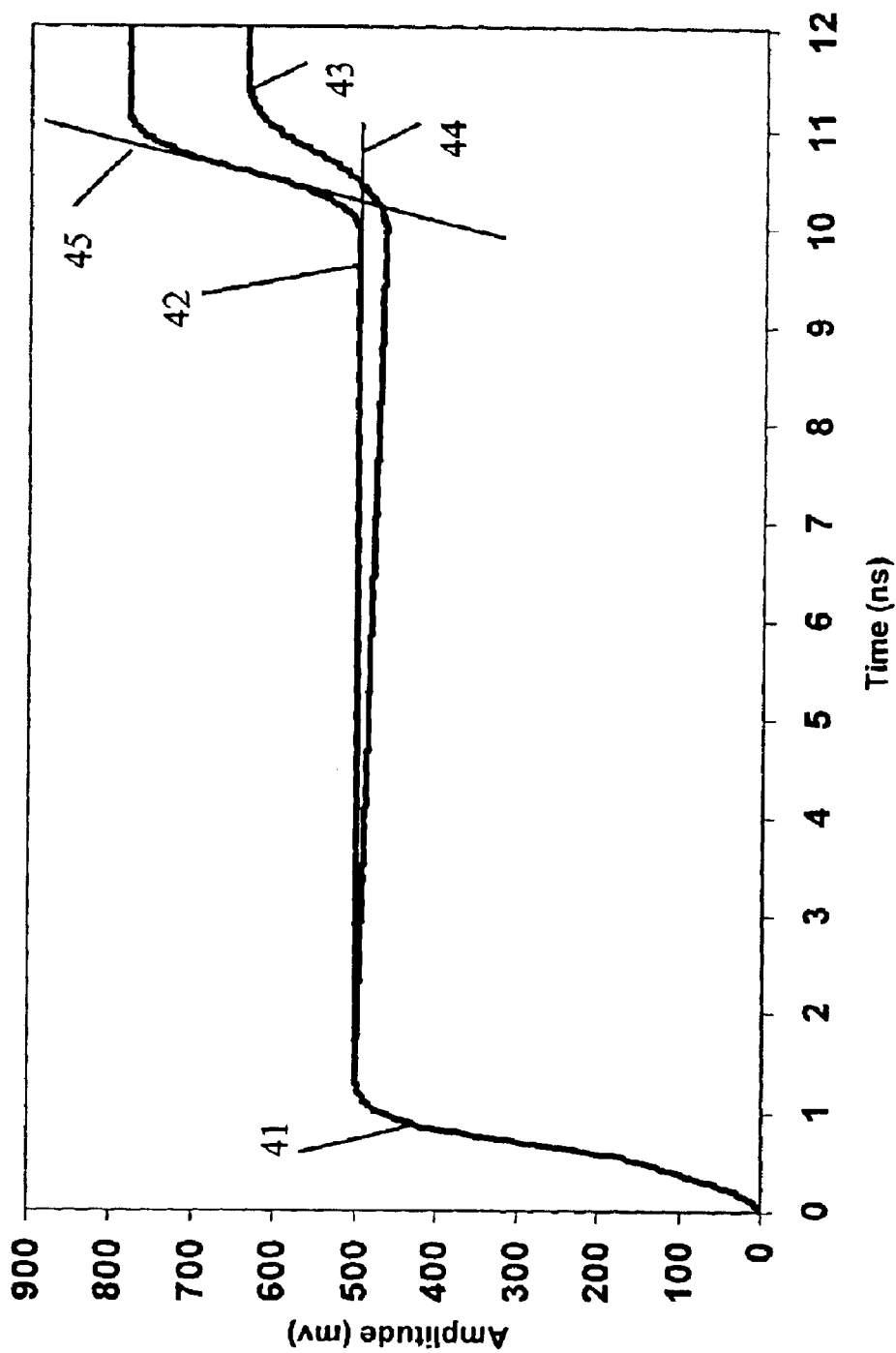
FIG. 4 shows typical waveforms encountered in a TDR sensor system with an open-ended transmission line.
Figure 5:
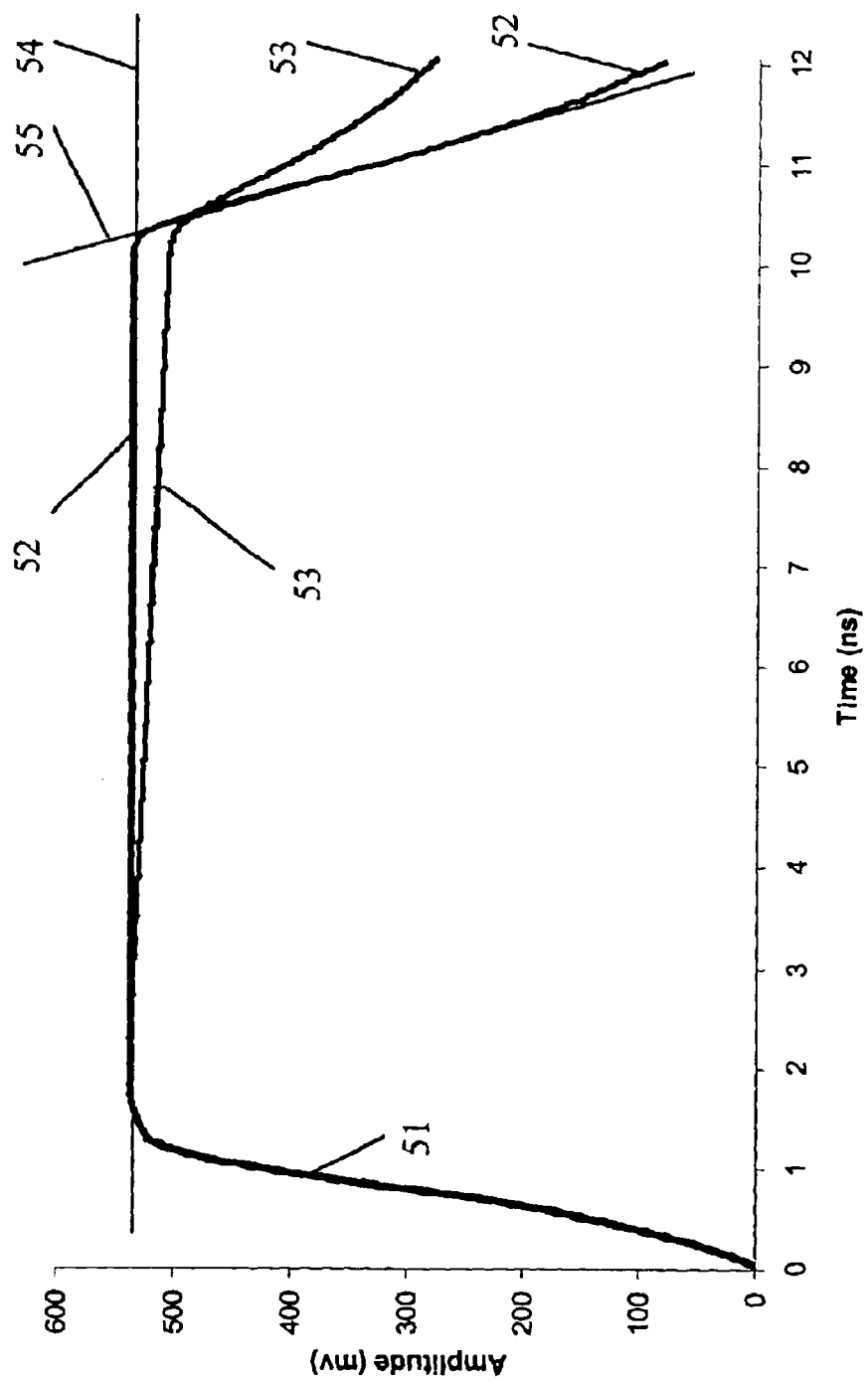
FIG. 5 shows typical waveforms encountered in a TDR sensor system with a shorted transmission line.

FIGS. 4 and 5 represent waveform measurements taken at successive time increments using the aforementioned process. In FIG. 4 transmitted waveform 41 represents the digitized waveform appearing at the driving/receiving end of an open-ended transmission line after a step function has been transmitted. The right-hand portion of the received waveform 42 represents the portion of the characteristic received waveform that has propagated through the moist media, reflected off of the open distal end of the transmission line 18 (FIG. 3), and returned to the point of origin. Note that this segment of received waveform 42 is a positive rising segment. For a shorted, rather than open, transmission line, refer to FIG. 5 where received waveform 52 with a negatively sloped segment is shown in response to transmitted waveform 51. Either case applies in this disclosure. The amplitude and slope of the segment of interest in received waveforms 42 and 52 are affected by the electrical conductivity of the medium in which the transmission line 18 is immersed. The timing of the rise of the segment of interest in received waveforms 42 and 52 are determined by the bulk dielectric constant of the medium. Note that in the apparatus described in '528, a low level signal preceded the waveform. This low signal represented residual feed-through due to the fact that the transmitter and receiver were housed on the same circuit board. When using the TDR method, the lead portion of the received waveform is identical to the transmitted waveform since the receiver is connected across the transmitter output terminals.

With increasing conductivity of the medium through which the characteristic received waveform propagates, the waveform will change from being like received waveform 42 to received waveform 43 in FIG. 4 for the case of an open-ended transmission line, or from 52 to 53 in FIG. 5 for a shorted transmission line. Note that received waveform 43 differs from received waveform 42 in that the rising edge slope is not as steep. However, the propagation times are nearly identical. This is expected since received waveforms 42 and 43 represent characteristic received waveforms that have propagated through soils or other media of equal wetness but different conductivities. Similar features will be noted in comparing received waveforms 52 and 53 with their negative sloping segments in FIG. 5 where received waveform 53 represents the signal returned through a medium that has higher conductivity.

The characteristic received waveform is analyzed to determine the bulk dielectric constant and the conductivity of the medium of interest through the following steps. First, the point of maximum slope of the reflected portion of the waveform is found from a mathematical analysis of the digitized waveform samples. This is done as in '528 by taking the mathematical derivative of a moving average of successive samples and locating the point of the maximum derivative. The timing, slope and amplitude of that point are retained. Next, the approximate point of upward inflection of the segment of interest in received waveform 42 (or downward inflection of 52) is determined through a search for the maximum second derivative of successive digitized waveform samples. Once that point is found a search is made for a zero-slope waveform segment just to the left of (prior to) the inflection point. The amplitude at that point represents the baseline amplitude above which the reflected wave rises (FIG. 4, line 44), or below which it drops (FIG. 5, line 54) depending upon whether transmission line 18 (FIG. 3) is open or shorted. The maximum slope, calculated earlier, is projected in line 45 (or 55) from its amplitude and timing coordinates onto this baseline 44 (or 54). The intersection of the slope 45 (or 55) with the baseline 44 (or 54) represents the propagation time. The slope (as in lines 45 and 55) of the segment of interest in received waveforms 42 and 52 can also be used to infer the conductivity of the medium.

The maximum slope of the characteristic received waveform is located in the same manner as described for the Bi-static approach. As mentioned in that earlier section, this method of extracting the salient features of the received waveform targets the peak of the transmitted energy being returned to the receiver, thus providing the greatest signal to noise ratio for accurate and repeatable measurements of the slope and timing.

The description here of alternate embodiments of a moisture sensor is in no way intended to suggest that these are the only embodiments available. It will be apparent to those of ordinary skill in the related arts that various combinations of the methods and configurations described here can be implemented in keeping with the intent of the disclosed invention and may have particular utility in some applications without departing from the spirit and scope of the invention as represented in the attached claims. Furthermore, the methods described for capturing, extracting and analyzing data are not meant to limit in any manner the application of the described invention.

Although the preferred embodiment has been generally described for measuring the moisture content and conductivity of soil, other embodiments may be adapted for similarly measuring those physical properties in many bulk materials. Some other media of interest where the present invention has been recognized as useful are grains held in storage as for cracking or milling, paper in its various forms whether during processing of the pulp or storage of the finished product in sheet or roll form, and lumber products in various forms. Other uses include the measurement of liquid levels in tanks, and the detection of moisture as a contaminant in fuel storage and engines.

What is claimed is:

1. A method for digitizing portions of a waveform sent through a moisture-bearing medium comprising the steps of:
   (a) providing an unshielded transmission line that passes through said medium to a latching comparator;
   (b) providing a shielded transmission line connected to said latching comparator;
   (c) launching a fast-transitioning waveform onto said unshielded transmission line;
   (d) measuring the amplitude of a resultant waveform at a programmed point in time at said latching comparator by using a technique involving generation of timing strobes in conjunction with a measurement of amplitude by successive approximation, said technique comprising the steps of:
      (d1) providing a programmable voltage reference to which said resultant waveform is compared by said latching comparator;
      (d2) providing a programmable time offset for generation of a precisely-timed sampling strobe after the launching of said fast-transitioning waveform in order to sample said resultant waveform amplitude at said latching comparator, said sampling strobe being sent through said shielded transmission line to said latching comparator;
      (d3) launching a multiplicity of said fast-transitioning waveform onto said transmission line and adjusting said programmable voltage reference in the manner of said successive approximation until an amplitude representative of a composite of resultant waveform at the given point in time has been acquired; and (d4) changing said programmable time offset to a next desired point in time and repeating steps d1 through d3 in order to acquire another amplitude representative of a multiplicity of resultant waveform at said next desired point in time until said portions of a waveform have been digitized.

2. The method in claim 1, wherein propagation time of said fast-transitioning waveform through said medium is calculated from said portions of a waveform, comprising the steps of:

(a) determining a characteristic slope of transition of said resultant waveform from a set of points within said portions of a waveform;

(b) locating a point of maximum slope of transition of said resultant waveform;

(c) projecting a straight line having said characteristic slope of transition through said point of maximum slope to a 0-Volt reference line; and (d) finding an intercept point of said straight line with said 0-Volt reference line, wherein the time associated with said intercept point represents said propagation time of said fast-transitioning waveform through said medium.

3. The method in claim 2, wherein said propagation time is used to calculate a value for the bulk dielectric constant of said medium in contact with said unshielded transmission line.

4. The method in claim 2, wherein said characteristic slope of transition of said resultant waveform is used to determine a value for the conductivity of said medium in contact with said unshielded transmission line.

5. The method in claim 1, wherein said medium is soil.

6. The method in claim 1, wherein said medium is bulk grain.

7. The method in claim 1, wherein said medium is bulk paper.

8. The method in claim 1, wherein said medium is lumber.

9. The method in claim 1, wherein said medium is a hydrocarbon fuel.

10. The method in claim 1, wherein said medium is oil.

11. A method for digitizing portions of a waveform sent through a moisture-bearing medium comprising the steps of:

(a) launching a fast-transitioning waveform onto a proximal end of a transmission line that passes through said medium to an open distal end of said transmission line;

(c) providing a latching comparator at said proximal end of said transmission line to receive a resultant waveform which contains a signal component that has been reflected from said open distal end;

(d) measuring the amplitude of said resultant waveform at a programmed point in time at said latching comparator by using a technique involving generation of timing strobes in conjunction with a measurement of amplitude by successive approximation, said technique comprising the steps of:

(d1) providing a programmable voltage reference to which said resultant waveform is compared by said latching comparator;

(d2) providing a programmable time offset for generation of a precisely-timed sampling strobe after said launching of said fast-transitioning waveform in order to sample said resultant waveform amplitude at said latching comparator;

(d3) launching a multiplicity of said fast-transitioning waveform onto said transmission line and adjusting said programmable voltage reference in the manner of said successive approximation until an amplitude representative of a composite of resultant waveform at the given point in time has been acquired; and (d4) changing said programmable time offset to a next desired point in time and repeating steps d1 through d3 in order to acquire another amplitude representative of a multiplicity of resultant waveform at said next desired point in time until said portions of a waveform have been digitized.

12. The method in claim 11, wherein propagation time of said fast-transitioning waveform through said medium is calculated from said portions of a waveform, comprising the steps of:

(a) determining a characteristic slope of transition from a subset of measured points which represent that portion of said resultant waveform which contains a signal component that has been reflected from said open distal end;

(b) locating a point of maximum slope of transition from within said subset of measured points;

(c) determining a baseline reference level from which said signal component that has been reflected from said open distal end rises;

(d) projecting a straight line having said characteristic slope of transition through said point of maximum slope to said baseline reference level; and (e) finding an intercept point of said straight line at said baseline reference level, wherein the time associated with said intercept point represents said propagation time of said fast-transitioning waveform through said medium.

13. The method in claim 12, wherein said propagation time is used to calculate a value for the bulk dielectric constant of the medium in contact with said transmission line.

14. The method in claim 12, wherein said characteristic slope of transition of said subset of measured points is used to determine a value for the conductivity of said medium in contact with said transmission line.

15. The method in claim 11, wherein said medium is soil.

16. The method in claim 11, wherein said medium is bulk grain.

17. The method in claim 11, wherein said medium is bulk paper.

18. The method in claim 11, wherein said medium is lumber.

19. The method in claim 11, wherein said medium is a hydrocarbon fuel.

20. The method in claim 11, wherein said medium is oil.

21. A method for digitizing portions of a waveform sent through a moisture-bearing medium comprising the steps of:

(a) launching a fast-transitioning waveform onto a proximal end of a transmission line that passes through said medium to a shorted distal end of said transmission line;

(c) providing a latching comparator at said proximal end of said transmission line to receive a resultant waveform which contains a signal component that has been reflected from said shorted distal end;

(d) measuring the amplitude of said resultant waveform at a programmed point in time at said latching comparator by using a technique involving generation of timing strobes in conjunction with a measurement of amplitude by successive approximation, said technique comprising the steps of:

(d1) providing a programmable voltage reference to which said resultant waveform is compared by said latching comparator;

(d2) providing a programmable time offset for generation of a precisely-timed sampling strobe after said launching of said fast-transitioning waveform in order to sample said resultant waveform amplitude at said latching comparator;

(d3) launching a multiplicity of said fast-transitioning waveform onto said transmission line and adjusting said programmable voltage reference in the manner of said successive approximation until an amplitude representative of a composite of resultant waveform at the given point in time has been acquired; and (d4) changing said programmable time offset to a next desired point in time and repeating steps d1 through d3 in order to acquire another amplitude representative of a multiplicity of resultant waveform at said next desired point in time until said portions of a waveform have been digitized.

22. The method in claim 21, wherein propagation time of said fast-transitioning waveform through said medium is calculated from said portions of a waveform, comprising the steps of:

(a) determining a characteristic slope of transition from a subset of measured points which represent that portion of said resultant waveform which contains a signal component that has been reflected from said shorted distal end;

(b) locating a point of maximum slope of transition from within said subset of measured points;

(c) determining a baseline reference level from which said signal component that has been reflected from said shorted distal end declines;

(d) projecting a straight line having said characteristic slope of transition through said point of maximum slope to said baseline reference level; and (e) finding an intercept point of said straight line at said baseline reference level, wherein the time associated with said intercept point represents said propagation time of said fast-transitioning waveform through said medium.

23. The method in claim 22, wherein said propagation time is used to calculate a value for the bulk dielectric constant of the medium in contact with said transmission line.

24. The method in claim 22, wherein said characteristic slope of transition of said subset of measured points is used to determine a value for the conductivity of said medium in contact with said transmission line.

25. The method in claim 21, wherein said medium is soil.

26. The method in claim 21, wherein said medium is bulk grain.

27. The method in claim 21, wherein said medium is bulk paper.

28. The method in claim 21, wherein said medium is lumber.

29. The method in claim 21, wherein said medium is a hydrocarbon fuel.

30. The method in claim 21, wherein said medium is oil.

* * * * *